(12) United States Patent
Bachur, Jr. et al.

(10) Patent No.: US 7,427,501 B2
(45) Date of Patent: Sep. 23, 2008

(54) SYSTEM AND METHOD FOR OPTICALLY MONITORING THE CONCENTRATION OF A GAS, OR THE PRESSURE, IN A SAMPLE VIAL TO DETECT SAMPLE GROWTH

(75) Inventors: Nicholas R. Bachur, Jr., Monkton, MD (US); Patrick S. Beaty, Felton, PA (US); Timothy G. Foley, Forest Hill, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/892,061

(22) Filed: Jun. 26, 2001

(65) Prior Publication Data

US 2003/0111607 A1    Jun. 19, 2003

Related U.S. Application Data

(60) Provisional application No. 60/236,164, filed on Sep. 29, 2000.

(51) Int. Cl.
   *C12M 1/34* (2006.01)
   *C12M 1/36* (2006.01)
(52) U.S. Cl. ............. 435/287.3; 435/287.5; 435/288.7; 435/808; 422/64; 422/65; 422/82.09; 250/328; 250/339.02; 250/339.05; 250/345; 356/437
(58) Field of Classification Search .................. 435/34, 435/286.2, 287.3, 287.5, 288.7, 808; 422/82.09; 436/165, 164; 250/328, 343; 356/437
See application file for complete search history.

(56) References Cited

U.S. PATENT DOCUMENTS 3,700,890 A * 10/1972 Kruezer .................... 250/341.1

(Continued)

FOREIGN PATENT DOCUMENTS

EP           151855 A1 *   8/1985

(Continued)

OTHER PUBLICATIONS

Allen. "Diode Laser Absorption Sensors For Gas Dynamic and Combustion Flow." Measurement Science and Technology. vol. 9 (1998), No. 4, pp. 545-562.*

(Continued)

*Primary Examiner*—William H Beisner

(57) ABSTRACT

A system and method employing infrared laser spectrography and dual wavelength modulation to monitor the concentration of a gas, such as oxygen or carbon dioxide, in the sample vial, or to monitor the pressure in the sample vial, to thus detect for microorganism growth in the sample vial. The system and method each employ an energy emitting device, such as an infrared laser, a detector and a signal analyzer, such as a spectroscopy device. The infrared laser emits toward the container infrared energy having a substantially single wavelength substantially equal to a wavelength at which the gas absorbs the infrared energy. The detector detects a portion of the energy signal that passes through the container, and the signal analyzer spectroscopically analyzes the detected portion of the energy signal to determine whether the gas exists in the container, or to determine the pressure in the container. The system and method thus determines whether an organism or cell of interest is present or viable in the container based on the results of the gas or pressure detection.

3 Claims, 14 Drawing Sheets

U.S. PATENT DOCUMENTS

| | | | | |
|---|---|---|---|---|
| 3,807,876 | A | * | 4/1974 | Nakahara et al. ............. 356/437 |
| 3,831,030 | A | * | 8/1974 | Wrobel et al. ......... 250/339.13 |
| 4,073,691 | A | * | 2/1978 | Ahnell et al. .................. 435/34 |
| 4,730,112 | A | * | 3/1988 | Wong .......................... 250/343 |
| 4,857,735 | A | * | 8/1989 | Noller ................... 250/339.07 |
| 4,889,992 | A | | 12/1989 | Hoberman .................. 250/343 |
| 4,945,060 | A | | 7/1990 | Turner |
| 4,952,498 | A | * | 8/1990 | Waters ......................... 435/34 |
| 5,094,955 | A | | 3/1992 | Calandra et al. |
| 5,155,019 | A | * | 10/1992 | Sussman et al. ............... 435/34 |
| 5,162,229 | A | | 11/1992 | Thorpe et al. |
| 5,164,796 | A | | 11/1992 | DiGuiseppi et al. |
| 5,217,876 | A | | 6/1993 | Turner et al. |
| 5,401,966 | A | | 3/1995 | Gray et al. |
| 5,473,161 | A | * | 12/1995 | Nix et al. .................... 250/343 |
| 5,482,842 | A | | 1/1996 | Berndt |
| 5,491,341 | A | * | 2/1996 | McCaul et al. ............... 250/343 |
| 5,518,923 | A | * | 5/1996 | Berndt et al. ............ 435/287.3 |
| 5,586,823 | A | | 12/1996 | Carr |
| 5,614,718 | A | * | 3/1997 | Brace .................... 250/339.13 |
| 5,742,399 | A | * | 4/1998 | McAndrew et al. ......... 356/437 |
| 5,856,175 | A | | 1/1999 | Thorpe et al. |
| 5,858,769 | A | | 1/1999 | DiGuiseppi et al. |
| 5,863,752 | A | | 1/1999 | Court et al. |
| 5,888,825 | A | * | 3/1999 | Carr et al. ...................... 436/48 |
| 5,930,000 | A | | 7/1999 | Brand |
| 6,064,488 | A | | 5/2000 | Brand et al. |
| 6,639,678 | B1 | * | 10/2003 | Veale ......................... 356/437 |

FOREIGN PATENT DOCUMENTS

| | | | |
|---|---|---|---|
| EP | 448923 | A1 * | 10/1991 |
| EP | 0 688863 | A2 | 12/1995 |
| EP | 0834554 | A2 | 4/1998 |
| GB | 2059574 | A | 4/1981 |

OTHER PUBLICATIONS

"Remote detection of methane with a 1.66-um diode laser" Kiyoji Uehara and Hidel Tai Feb. 20, 1992/vol. 31, No. 6, Applied Optics.

European Search Report-EP 01 12 2846), Dec. 29, 2003.

* cited by examiner

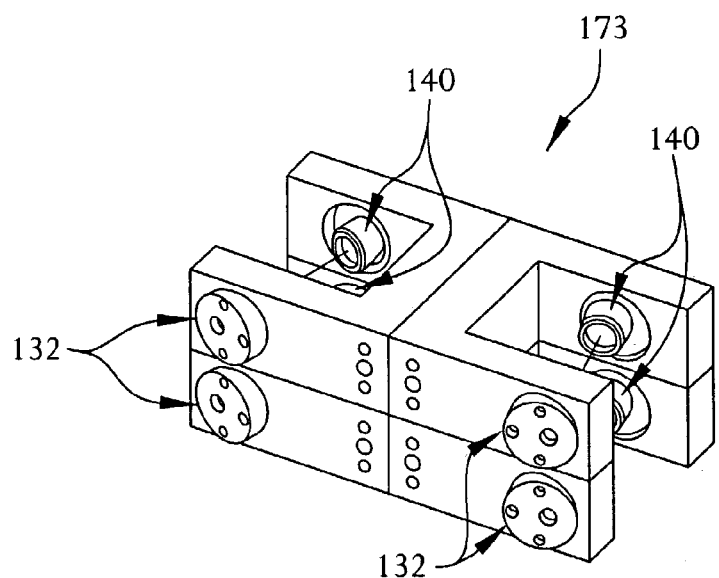
FIG. 12
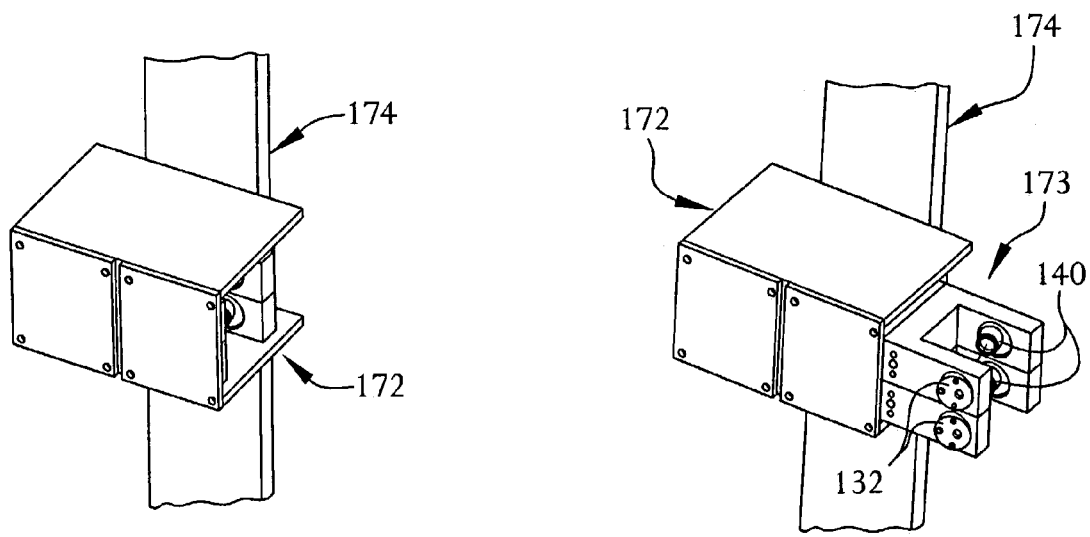
FIG. 14
FIG. 15

US 7,427,501 B2

SYSTEM AND METHOD FOR OPTICALLY MONITORING THE CONCENTRATION OF A GAS, OR THE PRESSURE, IN A SAMPLE VIAL TO DETECT SAMPLE GROWTH

The present application claims benefit under 35 U.S.C. § 119(e) of a U.S. Provisional Patent Application No. 60/236,164, filed Sep. 29, 2000, the entire contents of which is incorporated herein by reference.

CROSS-REFERENCE TO RELATED APPLICATIONS

Related subject matter is disclosed in a U.S. Patent Application of Nicholas R. Bachur, Jr. entitled "System and Method for Optically Monitoring the Concentration of a Gas in a Sample Vial Using Photothermal Spectroscopy to Detect Sample Growth", the entire contents of which is incorporated herein by reference.

BACKGROUND OF THE INVENTION

1. Field of the Invention

The present invention relates to a system and method for optically monitoring the concentration of a gas, or the pressure, in a sample vial to detect the presence of sample growth. More particularly, the present invention relates to a system and method employing infrared laser spectroscopy and dual wavelength modulation to monitor the concentration of a gas, such as oxygen or carbon dioxide, in the sample vial, or to monitor the pressure in the sample vial, to thus detect for microorganism growth in the sample vial.

2. Description of the Related Art

Many medical diagnoses require that a fluid sample, such as a blood sample, be taken from a patient, cultured in a growth medium, and then examined for the presence of a pathogen believed to be causing the patient's illness. The growth medium provides nutrients that allow the pathogen, such as a bacteria, virus, mycobacteria, mammalian cells or the like, to multiply to a sufficient number so that their presence can be detected.

In some cases, the pathogen can multiply to a large enough number so that it can be detected visually. For example, a portion of the culture can be placed on a microscope slide, and visually examined to detect for the presence of a pathogen of interest.

Alternatively, the presence of a pathogen or other organism can be detected indirectly by detecting for the presence of byproducts given off by the microorganism during its growth. For example, certain microorganisms such as mammalian cells, insect cells, bacteria, viruses, mycobacteria and fungi consume oxygen during their growth and life cycle. As the number of microorganisms increases in the sample culture, they naturally consume more oxygen. Furthermore, these oxygen consuming organisms typically release carbon dioxide as a metabolic byproduct. Accordingly, as the number of organisms present increases, the volume of carbon dioxide that they collectively release likewise increases.

Several methods exist for detecting the presence of carbon dioxide in a sample to determine whether organisms are present in the sample. For example, an instrument known as the Bactec® 9050 manufactured by Becton Dickinson and Company detects for the change in color of an indicator to determine whether carbon dioxide is present in a sample. That is, each sample is collected in a respective sample vial containing an indicator medium having a chemical that reacts in the presence of carbon dioxide to change color. A light sensor detects the color of the indicator medium in the sample vial when the sample vial is loaded into the instrument. If the sample contains an organism which emits carbon dioxide, the reflected or fluorescent intensity of the indicator medium will change in response to the presence of carbon dioxide. The light sensor will therefore detect this change in intensity, and the instrument will thus indicate to an operator that an organism is present in the sample contained in the sample vial. Other examples of instruments for detecting the presence of organisms in a sample by detecting for the change in carbon dioxide in the sample are described in U.S. Pat. Nos. 4,945,060, 5,164,796, 5,094,955 and 5,217,876, the entire contents of each of these patents are incorporated herein by reference.

Alternatively, instead of detecting for the presence of carbon dioxide to detect the presence of an oxygen consuming microorganism, it is possible to detect for a depletion in the concentration of oxygen in the sample of interest. In such a system, the sample vial includes an indicator whose color or fluorescence changes as the concentration of oxygen in the vial changes. This change in color or fluorescence can be detected by an instrument, which can provide an indication to a technician that oxygen in the sample is being depleted by an oxygen consuming organism within the sample. An instrument employing this oxygen detecting technique is described in U.S. Pat. No. 5,567,598, the entire contents of which are incorporated herein by reference.

The presence of oxygen consuming organisms can also be detected by detecting for a change in pressure in a sealed sample vial containing the sample of interest. That is, as oxygen in a closed sample vial is depleted by oxygen consuming organisms, the pressure in the sealed sample vial will change. The pressure will further change in the sample vial as the organisms emit carbon dioxide. Therefore, the presence of such organisms can be detected by monitoring for a change in pressure in the closed sample vial. Instruments that are capable of detecting changes in pressure in the sample vial are described in U.S. Pat. Nos. 4,152,213, 5,310,658, 5,856,175 and 5,863,752, the entire contents of each of these patents are incorporated herein by reference.

It is noted that the techniques described above each detect for the presence of oxygen or carbon dioxide in a sample vial by detecting the change in a state or condition of an indicator other than the oxygen or carbon dioxide itself. For example, certain of the techniques detect for a change in color of an indicator, while others detect for a physical change, such as the movement of a diaphragm which indicates a change in pressure. These techniques can therefore be susceptible to erroneous results if, for example, the indicators themselves are inaccurate.

Accordingly, to avoid such errors, detection probes or sensors can be inserted directly into the sample vial to detect for the presence of carbon dioxide or oxygen directly. An instrument for detecting for the presence of carbon dioxide in a sample directly is described in U.S. Pat. No. 4,971,900, the entire contents of which are incorporated herein by reference. This probe technique, however, is an invasive technique which requires that a sensor or probe be inserted directly into the sample vial containing the sample. This technique can prove hazardous because the probes can become contaminated with the organism present in the sample. Moreover, when the probes are being inserted into or removed from the vial, the potentially hazardous organisms can escape into the atmosphere, thus endangering the technician or others in the general vicinity of the instrument.

Techniques have therefore been developed which are capable of detecting the presence of, for example, carbon dioxide without the need for detecting a change in the condition of an indicator, and without the use of an invasive detector or probe. In one technique, infrared light is irradiated through the sample vial containing the sample of interest. The infrared light passing through the sample vial is detected by an infrared detector. Because carbon dioxide absorbs infrared light within a certain wavelength range, if any carbon dioxide is present in the sample vial, infrared light within that particular wavelength range will be absorbed by the carbon dioxide and thus not be detected by the infrared detector. The signals from the infrared detector are analyzed to determine whether any of the infrared light being emitted into the sample vial is absorbed and thus not detected by the infrared detector. If any absorption has occurred, the instrument provides an indication that carbon dioxide is present in the sample vial, and thus, a carbon dioxide producing organism is likely present. Examples of instruments which perform this type of technique are described in U.S. Pat. Nos. 5,155,019, 5,482,842 and 5,427,920, the entire contents of each are incorporated by reference herein.

The infrared light detecting technique has advantages over the technique described above which uses an invasive detector or probe, because the technique reduces the possibility of contamination. Furthermore, because the infrared light technique directly detects for the presence of carbon dioxide instead of detecting for a change in an indicator, more accurate results can be attained. However, the infrared light technique has certain disadvantages. For example, carbon dioxide absorbs infrared light within a somewhat wide range of wavelength, which can also be absorbed by other gases. Hence, if gases in the vial other than carbon dioxide absorb some of the infrared light, the instrument may provide a false indication that carbon dioxide is present Accordingly, the accuracy of the infrared light technique described in the patents referenced above is somewhat limited.

A need therefore exists for an improved non-invasive system and method for detecting for the presence of oxygen or carbon dioxide in a culture sample, to thus detect for the presence of an oxygen consuming or carbon dioxide producing organism in the sample.

SUMMARY OF THE INVENTION

An object of the present invention is to provide an improved system and method for optically monitoring the concentration of a gas, or the pressure, in a sample vial to detect the presence of sample growth.

Another object of the present invention is to provide a system and method employing infrared laser spectrography and dual wavelength modulation to monitor the concentration of a gas, such as oxygen or carbon dioxide, in the sample vial, or to monitor the pressure in the sample vial, to thus detect for microorganism growth in the sample vial.

A further object of the present invention is to provide a system and method capable of housing and incubating multiple sample vials containing respective samples, and optically monitoring the concentration of a gas, or the pressure, in each of the sample vials to detect the presence of sample growth in the vials.

These and other objects are substantially achieved by providing a system and method for monitoring the concentration of a gas, such as oxygen or carbon dioxide, in a container, or for monitoring the pressure in a container. The system and method each employ an energy emitting device, such as an infrared laser, a detector and a signal analyzer, such as a spectroscopy device. The infrared laser emits toward the container infrared energy having a wavelength substantially equal to a wavelength at which the gas absorbs the infrared energy. The detector detects a portion of the energy signal that passes through the container, and the signal analyzer spectroscopically analyzes the detected portion of the energy signal to determine whether the gas exists in the container. The system and method thus determines whether an organism of interest is present in the container based on the results of the gas or pressure detection.

BRIEF DESCRIPTION OF THE DRAWINGS

These and other objects, advantages and novel features of the invention will be more readily appreciated from the following detailed description when read in conjunction with the accompanying drawings, in which:

FIG. 12 is a top view of the instrument shown in FIG. 2 including the monitoring assembly shown in FIGS. 10 and 11;

FIG. 14 is a detailed view illustrating the sensor head shown in FIG. 12 retracted into the sensor head housing of the monitoring assembly shown in FIGS. 10 and 11;

FIG. 15 is a detailed view showing the sensor head shown in FIG. 12 extended from another end of the sensor head housing of the monitoring assembly shown in FIGS. 10 and 11;

DETAILED DESCRIPTION OF THE PREFERRED EMBODIMENTS

Figure 1:
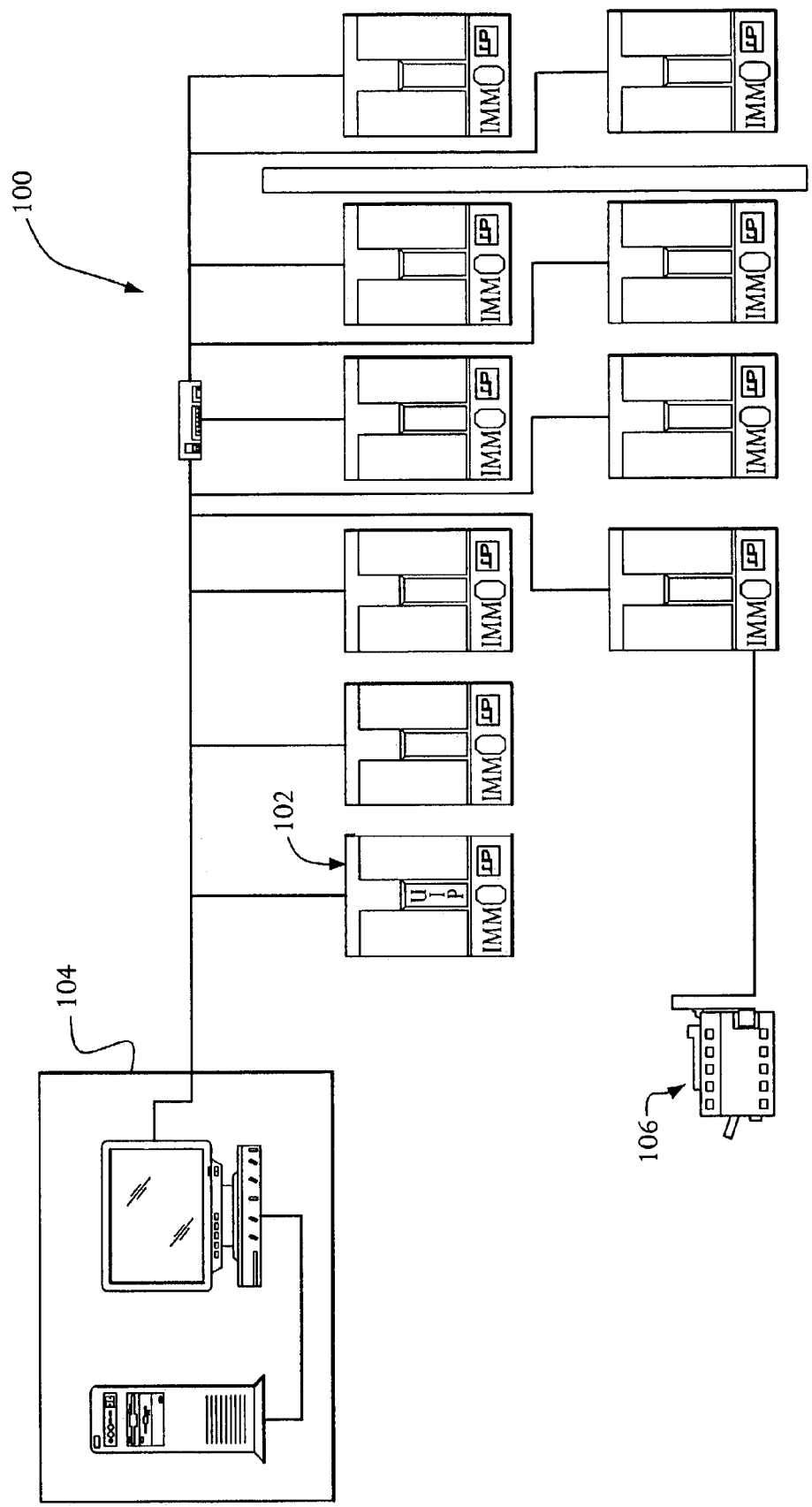
FIG. 1 is a block diagram of a system employing multiple incubation and measurement instruments according to an embodiment of the present invention, which each use infrared laser spectrography and dual wavelength modulation techniques to monitor the concentration of a gas, such as oxygen or carbon dioxide, in sample vials, or to monitor the pressure in the sample vials, to thus detect for microorganism growth in the sample vials.
Figure 2:
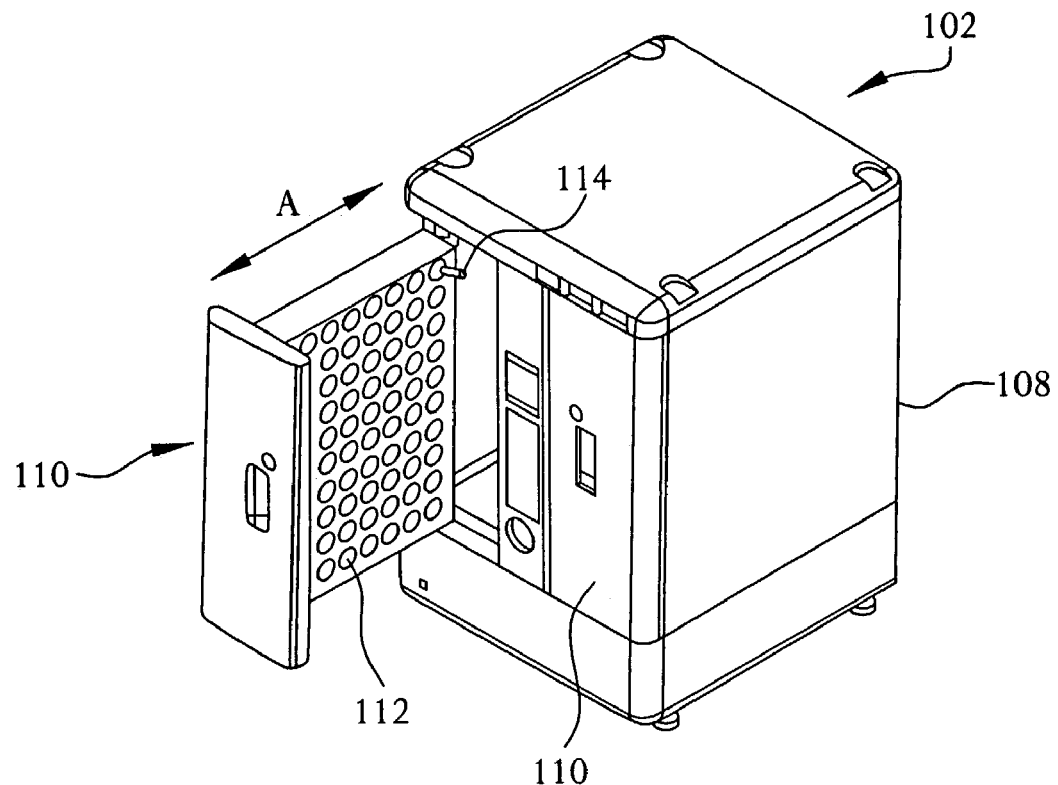
FIG. 2 is a detailed view of an instrument employed in the system shown in FIG. 1.

A system 100 for detecting growth of microorganisms in sample cultures according to an embodiment of the present invention is shown in FIG. 1. As illustrated, the system 100 includes a plurality of incubation and measurement modules 102 that are connected to a central computer 104. The central computer 104 can control the incubation temperatures and times, as well as the timing of the measurements performed by the modules 102, and can collect and classify the data readings obtained by the modules 102. The system 100 can also include a data output device, such as a printer 106, that can be controlled by the central computer 104 to print data readings obtained by the incubation and measurements modules 102.

Further details of the incubation and measurement modules 102 are shown in FIGS. 2-7. As illustrated, each incubation and measurement module 102 in this example includes a housing 108 and two shelves 110 that can be slid into and out of the housing 108 in a direction along arrow A. Each shelf 110 includes a plurality of openings 112, each of which is adapted to receive a sample vial 114. The openings 112 are arranged in a plurality of rows and columns as shown, and each shelf 110 can have any practical number of openings. For example, the openings 112 can be arranged in nine rows, with nine columns in each row, thus totaling 81 openings 112 per shelf 110.

When a sample culture is to be analyzed by the incubation and measurement module 102, the sample culture is placed in a sample vial 114, and the sample vial 114 is loaded into a respective opening 112 in the incubation and measurement module 102. The sample vial 114 is a closed sample vial in this example. The incubation and measurement module 102 can further include a keyboard, a barcode reader, or any other suitable interface that enables a technician to enter information pertaining to the sample into a database stored in a memory in the incubation and measurement module 102, in the central computer 104, or both. The information can include, for example, patient information, sample type, the row and column of the opening 112 into which the sample vial 114 is being loaded, and so on.

Figure 3:
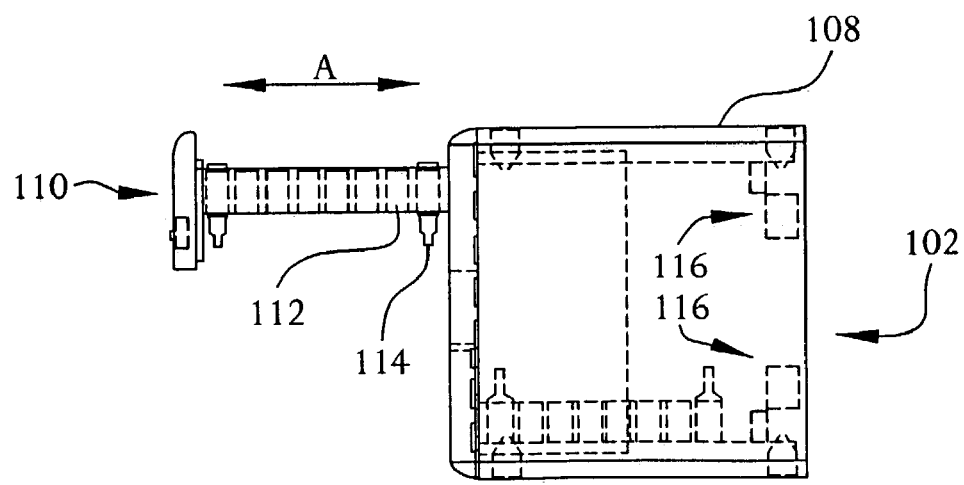
FIG. 3 is a top view of the instrument shown in FIG. 2.
Figure 4:
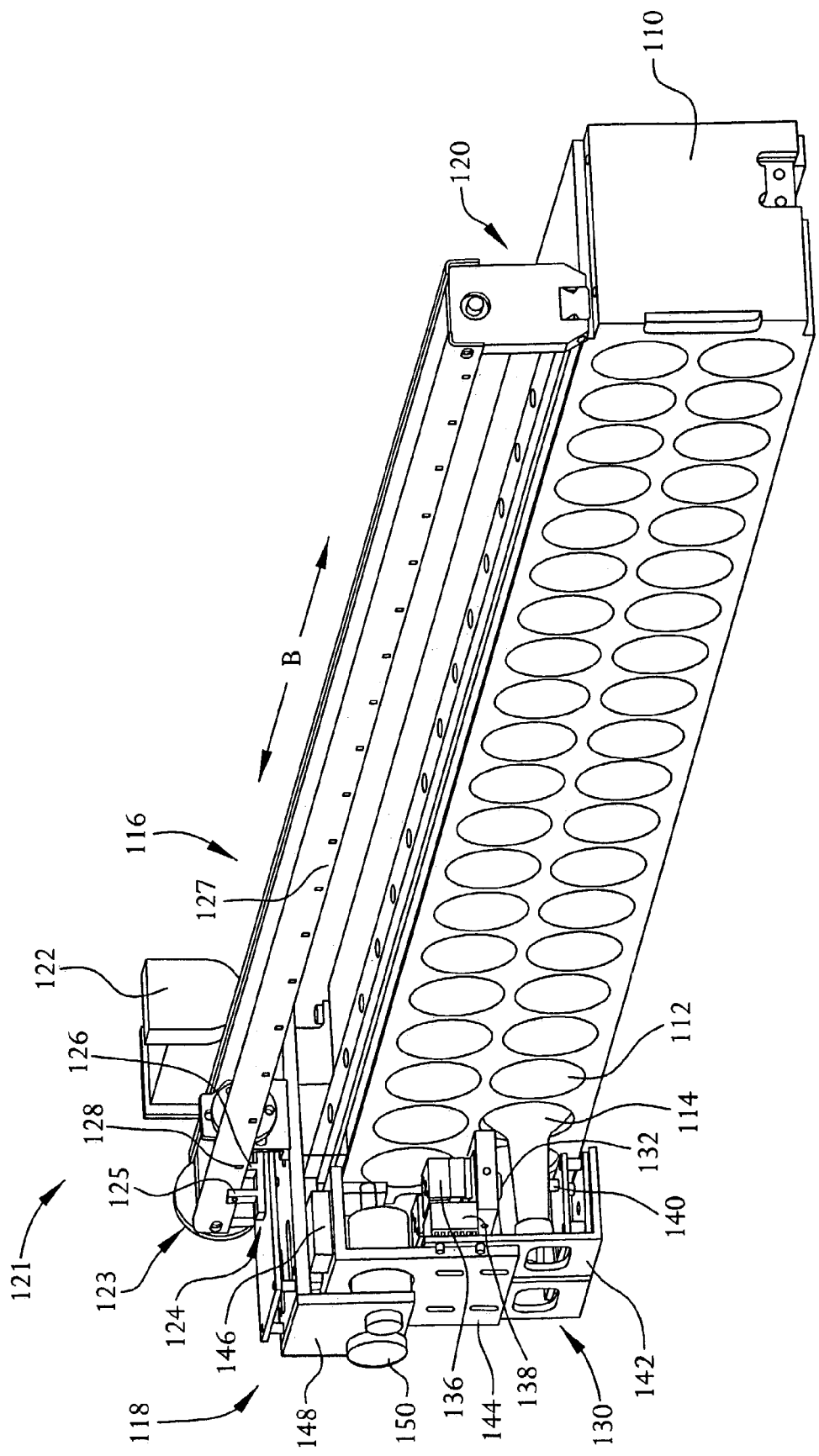
FIG. 4 is a detailed view of an example of a detector assembly employed in the instrument shown in FIGS. 1-3 which uses infrared laser spectrography and dual wavelength modulation techniques to monitor the concentration of a gas or the pressure in the sample vials.
Figure 5:
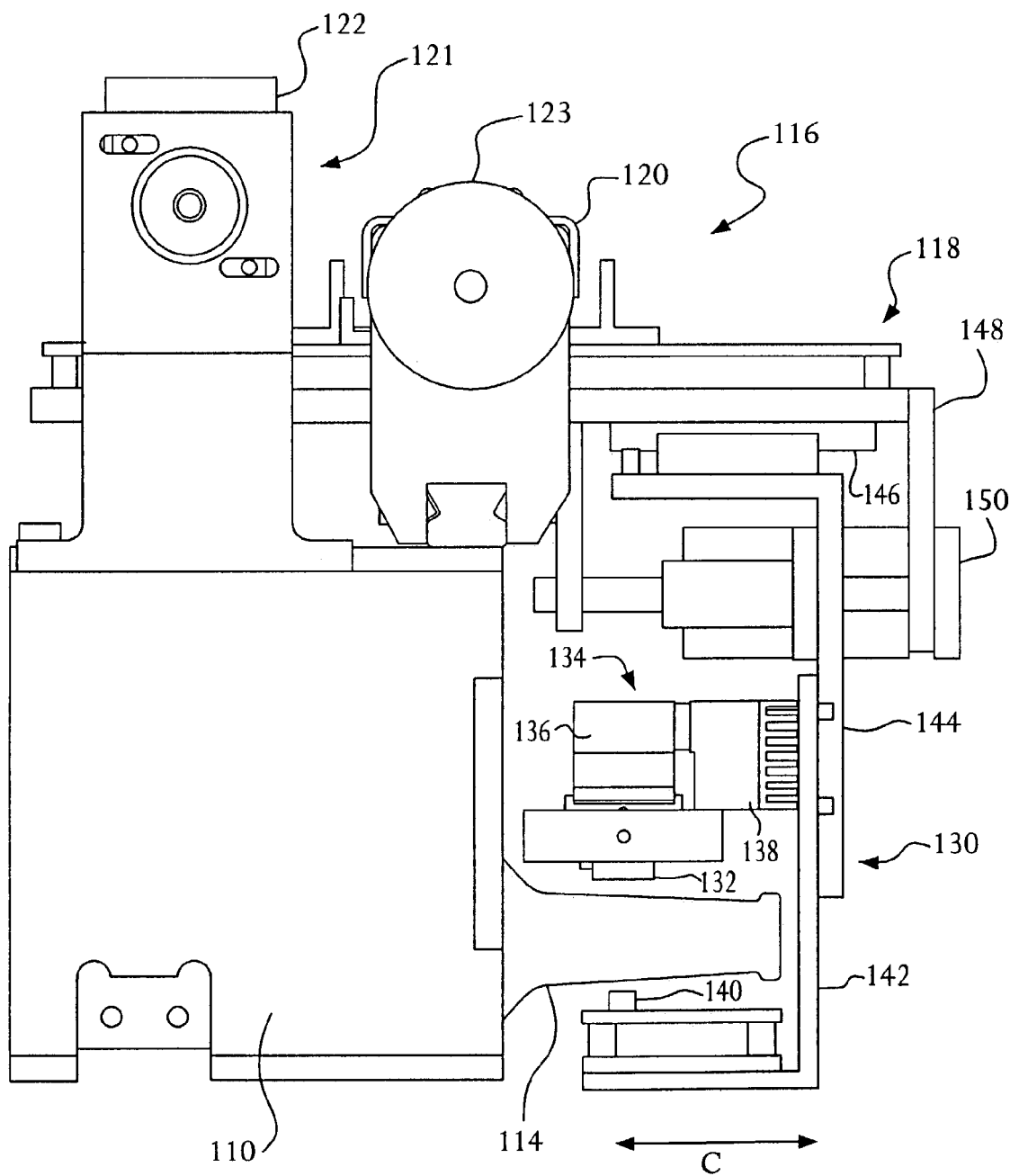
FIG. 5 is a side view of the monitoring assembly taken along lines 5-5 in FIG. 4.
Figure 6:
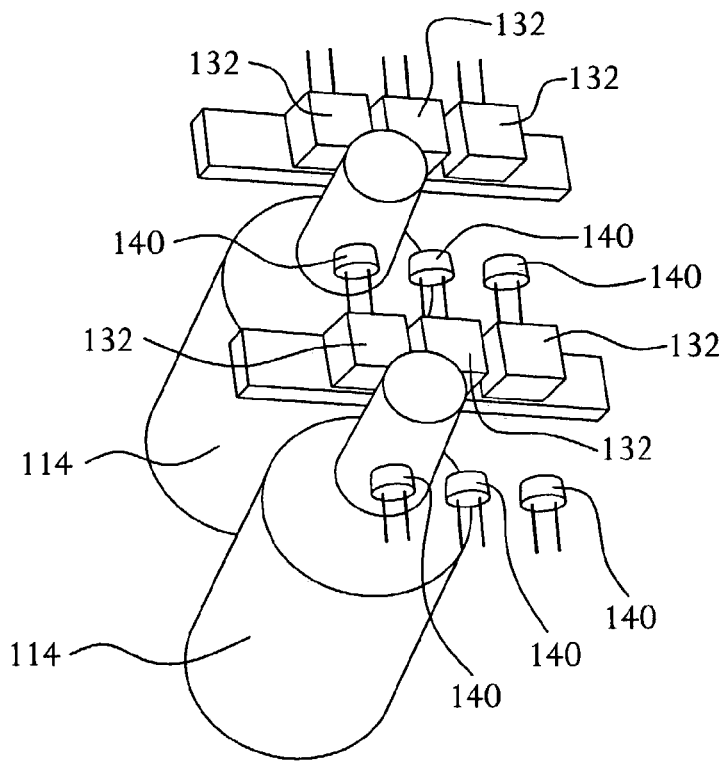
FIG. 6 is a conceptual view of a multiple laser and multiple detector arrangement employed in the monitoring assembly shown in FIGS. 4 and 5.

As further shown in FIG. 3, and is shown in more detail in FIGS. 4-6, the incubation and measurement module 102 includes a plurality of monitoring assemblies 116, which are positioned in the incubation and measurement modules 102 to obtain readings from the sample vials 114. In the example shown in FIGS. 4 and 5, each monitoring assembly 116 is configured to obtain measurements from sample vials 114 inserted in two rows of openings 112. However, the monitoring assembly 116 can be configured to obtain readings from sample vial 114 in any number of rows of openings 112 as desired.

The monitoring assembly 116 includes a movable assembly 118 which, in this example, is slidably coupled to a rail assembly 120 which is fixedly coupled to the top portion of shelf 110. A motor and pulley assembly 121 comprising a motor 122, such as a D.C. servo motor, and a pulley arrangement 123 that is driven by the motor 122, is coupled to the rail assembly 120 and movable assembly 118. The motor 122 is controlled by, for example, central computer 104 or a computer in incubation and measurement module 102 to drive the pulley arrangement 123 which, in response, drives movable assembly 118 to slide along rail assembly 120 in a sample vial reading direction indicated by arrow B in FIG. 4.

Moveable assembly 118 in this example also includes a sensor 124 that can include, for example, a light emitting device 125 and light sensing device 126 positioned on opposite sides of a rail 127 of rail assembly 120. As the motor and pulley assembly 121 drives the moveable assembly 118 along rail assembly 120, the sensor 124 detects the openings 128 in the rail 126, and provides a signal indicative of this detection to central computer 104 or a computer in the incubation and measurement module 102. The central computer 104 or a computer in the incubation and measurement module 102 uses this detection signal to monitor the position of the moveable assembly 118 along rail assembly 120. Also, because each opening 128 corresponds to a respective column of opening 112 in the shelf 110, the computer can determine which sample vials 114 are being read by the detectors in the moveable assembly 118 of monitoring assembly 116 as will now be described.

Moveable assembly 118 can include a plurality of detector units 130, the number of which corresponds to the number of rows of sample vials 114 that the monitoring assembly 116 is configured to read. That is, if the monitoring assembly 116 is configured to read two rows of sample vials 114, the movable assembly 118 will include two detector units 130. For illustration purposes, FIGS. 4 and 5 show only one detector unit 130.

In an alternate arrangement, movable assembly 118 can be configured to scan in an x-y direction to take readings from the sample vials 114. That is, the movable assembly 118 can be configured to scan back and forth along the rows of sample vials 114 to therefore take readings from the entire array of sample vials 114.

As shown in FIGS. 4 and 5, each detector unit 130 includes at least one laser 132 which, in this example, is an infrared diode laser. The laser 132 is coupled to a laser assembly 134, which includes a cooling and heating device 136 that can cool or heat the laser 132 to tune the frequency of the light being emitted by the laser 132. In other words, because the laser 132 emits light having a single frequency, a controller (e.g., controller 154 shown in FIG. 7 and described below) can control the cooling and heating device 136 to change this frequency, thus enabling the laser 132 to scan a range of frequencies. The laser assembly 134 further includes a heat sink 138 that can dissipate heat from the cooling and heating device 136, and thus aid in controlling the temperature of the laser 132.

As further illustrated, each detector unit 130 includes a detector 140 that is mounted to receive the laser light being emitted by laser 132. In this example, detector 140 is an infrared light detector capable of detecting infrared light having the wavelength of the light emitted by laser 132. The laser 132, laser assembly 134, and detector 140 are coupled to a laser and detector mounting bracket 142, that is further coupled to a movable mounting bracket 144. The movable mounting bracket 144 is coupled along slide rails 146 to a fixed mounting bracket 148, which is coupled to rail assembly 120 for movement along rail assembly 120 by motor and pulley assembly 121. A motor 150 is coupled to movable mounting bracket 144 and is controlled by central computer 104 or a computer in the incubation and measurement module 102 to move the movable mounting bracket 144 in a direction along arrow C as shown in FIG. 5. The motor 150 can thus position laser 132 and detector 140 at the appropriate location along the neck of sample vial 114 to obtain the most accurate readings as discussed in more detail below. Also, as can be appreciated from the above description, by moving the fixed mounting bracket 148 along rail assembly 120, the motor and pulley assembly 121 translates the entire movable assembly 118 including the laser 132 and detector 140 along the direction B in FIG. 4. This movement thus positions the laser 132 and detector 140 at the necks of the sample vials 114 in the row of sample vials 114.

In addition, for illustration purposes, FIGS. 4 and 5 each show only a single laser 132 and a single detector 140. However, as shown conceptually in FIG. 6, the laser and detector mounting bracket 142 can have a plurality of lasers 132 and a plurality of detectors 140 mounted thereto. In FIG. 6, three lasers 132 and three corresponding detectors 140 are shown. As described in more detail below, each laser 132 can emit infrared light having a particular wavelength based on the type of gas that is to be detected in the sample vials 114. For example, one laser 132 can emit infrared laser light having a wavelength appropriate for detecting carbon dioxide, another laser 132 can emit infrared laser light having a wavelength appropriate for detecting oxygen, and the third laser 132 can emit infrared laser light having a wavelength appropriate for detecting another type of gas. Also, each detector 140 is positioned to detect light from a respective laser 132 as shown.

Figure 7:
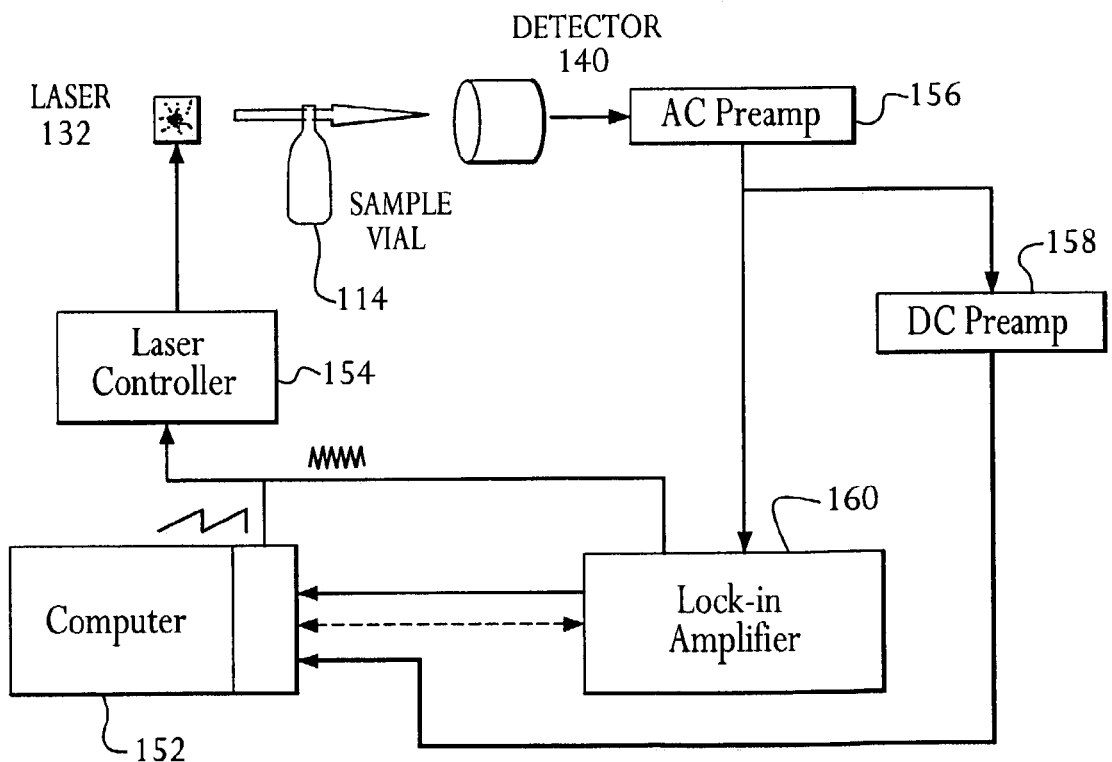
FIG. 7 is a block diagram of an example of electronic components used by the monitoring assembly to monitor the concentration of one or more gasses or the pressure in the sample vials.

FIG. 7 is an exemplary schematic illustrating components for reading a sample vial 114. As shown, once a laser 132 and corresponding detector 140 have been positioned with respect to a sample vial 114 to be read, a computer 152, which can be included in central computer 104 or in incubation and measurement module 102, controls a laser controller 154 to control laser 132 to emit infrared laser light toward the neck of the sample vial 114. The laser light that passes through sample vial 114 is detected by detector 140, which converts the detected laser light into an electrical signal and provides the electrical signal to an AC preamplifier 156. As can be appreciated by one skilled in the art, the AC preamplifier 156 performs an AC amplification on the electrical signal and provides the amplified signal to a DC preamplifier 158 and a lock-in amplifier 160. The DC preamplifier 158 and the lock-in amplifier 160 further amplify the electrical signal and provide the further amplified electrical signal to the computer 152.

The computer 152 interprets the amplified signal to determine whether any of the infrared laser light emitted by laser 132 has not been detected by detector 140, thus indicating that some of the laser light has been absorbed by a gas within the sample vial 114. The computer 152 can therefore determine the type and concentration of the gas and, if desired, the pressure inside the sample vial 114 based on the amplified electrical signal as will now be described in detail.

As stated above, the incubation and measurement module 104 employs an infrared diode laser spectroscopy technique to quantify the concentration of a gas of interest, such as carbon dioxide gas, oxygen gas, $NH_3$, $H_2S$, $CH_4$ or $SO_2$, in the head space above a liquid growth medium in the sample vials 114 to detect a microorganisms' metabolic activity. As can be appreciated by one skilled in the art, some organisms are more easily detected by detecting gas phase carbon dioxide rather than dissolved carbon dioxide. When the incubation and measurement module 104 is being operated to detect gas phase carbon dioxide in the sample vials 114, either the central computer 104 (FIG. 1), computer 152 (FIG. 7) or another computer in the incubation and measurement module 102 (hereinafter "the reading controller") controls the motor and pulley assembly 121 to move the movable assembly 118 past the sample vials 114 in a direction along arrow B (FIG. 4).

When the computer 152 determines, based on a detection signal provided by sensor 125, that the laser 132 for detecting carbon dioxide gas is positioned at the appropriate location with respect to a first sample vial 114 to be read, computer 152 controls the laser 132 to emit infrared laser light at an output wavelength within a discrete band of wavelength that can be absorbed by carbon dioxide. In this example, the wavelength of the emitted infrared laser light is in the 2.004 micrometer band. Lasers 132 can be a DFB diode laser IR source, which is monomodal and fairly inexpensive. It is also noted that various types of lasers and other electromagnetic energy sources can be used to analyze absorption and Raman spectroscopic data at various wavelengths. Also, detectors 140 can include, for example, photodiodes, electron multipliers, photomultipliers, and CCD or CMOS imagers, to name a few.

It is also noted that to detect different types of gasses, lasers which emit light having wavelengths appropriate for detecting those gasses are employed in the detector unit 130. For example, to detect $NH_3$, a laser 132 that emits light in the 1.997 micrometer band is used. To detect $H_2S$, a laser 132 that emits light in the 1.570 micrometer band is used, to detect $CH_4$, a laser that emits light in the 1.650 micrometer band is used, and to detect $SO_2$, a laser that emits light in the 7.28 micrometer band is used.

The infrared laser light thus passes through an enclosed volume of gas contained in the sample vial 114 in the area of the interior of the sample vial 114 above the microbial culture media. The computer 152 controls the detector 140 associated with laser 132 to detect the infrared laser light that passes through the sample vial 114. As described above, the detector 140 converts the detected infrared light into signals that are amplified by AC preamplifier 156, DC preamplifier 158 and lock-in amplifier 160, and then provided to computer 152.

Figure 8:
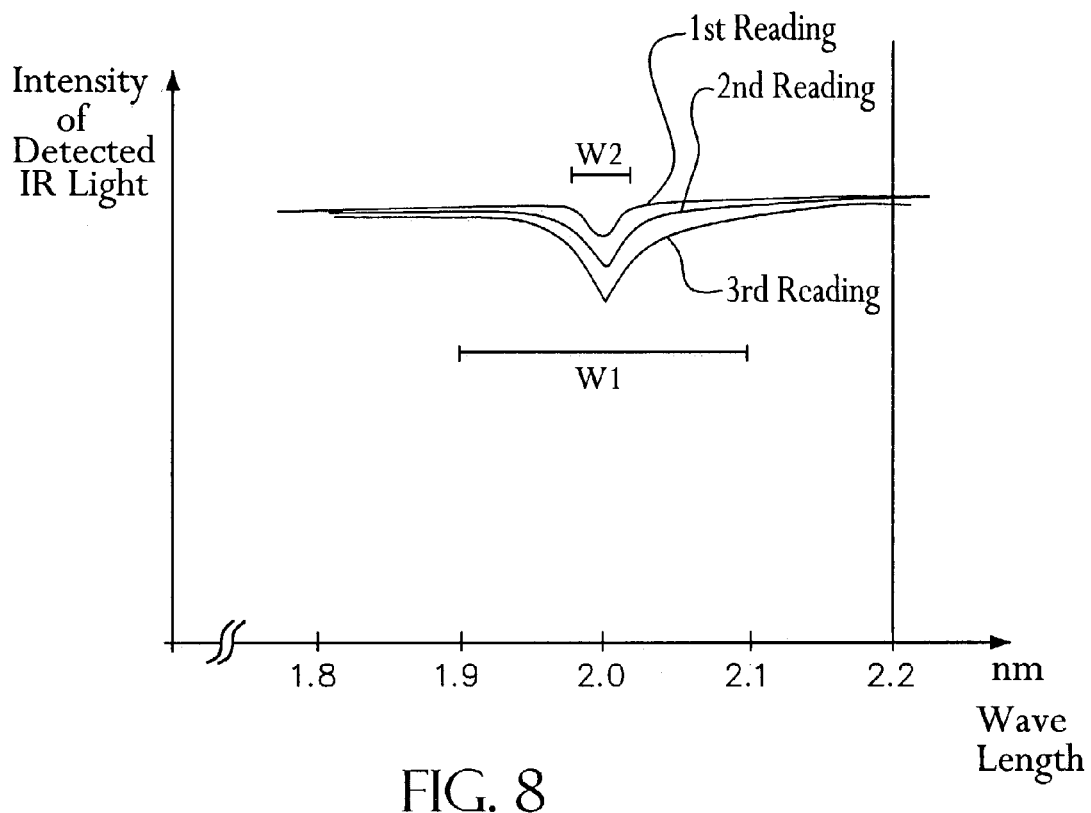
FIG. 8 is a graph illustrating an example of the intensity of the energy passing through the sample vial that is detected by the detector versus the wavelength of the detected energy, with an absorption peak being present at the wavelength at which carbon dioxide absorbs the energy.

The computer 152 can represent the detected infrared signal graphically as shown in FIG. 8, with the detected intensity on the vertical axis versus wavelength on the horizontal axis. To obtain the graph shown in FIG. 8, the computer 152 can employ any of the dual wave modulation spectroscopy techniques described, for example, in U.S. Pat. Nos. 4,934,816, 5,015,848, 5,804,702, 5,969,825, 5,973,782, 5,570,697, 4,509,130, 5,640,245, 5,742,399, 5,491,341, 5,636,035, 4,937,448 and 5,173,749, the entire contents of each of these patents are incorporated by reference herein. These discrete near infrared scanning techniques eliminate or at least minimize problems associated with poor signal to noise ratios present in previous techniques, such as those described in U.S. Pat. Nos. 5,155,019, 5,482,842 and 5,427,920 referenced above. In addition, the technique can employ various types of signal processing techniques, such as frequency or wavelength modulation, statistical curve fitting, digital signal processing, detector output algorithms and others to determine true signal from background noise and artifacts. Other techniques such as gas absorption spectroscopy, Raman spectroscopy, diode laser spectroscopy, or infrared spectroscopy, can also be used.

The reading controller then controls the motor and pulley assembly 121 to translate movable assembly 118 along rail assembly 120 to obtain readings from all the sample vials 114 in a manner similar to that described above. As the readings are being taken, the computer 152 can represent each of the respective detected infrared signals for each respective vial 114 graphically as described above.

After a predetermined period of time has elapsed from the initial readings, the reading controller then controls the motor and pulley assembly 121 to translate movable assembly 118 along rail assembly 120 to obtain a second set of readings from all the sample vials 114 in a manner similar to that described above. The computer 152 can graphically represent these second readings with respect to each sample vial 114 in the manner as described above. The reading controller can continue to control movement of the movable assembly 118 to take additional readings of the sample vials 114 at desired intervals in time. As the readings are taken, levels of carbon dioxide concentration and change over time related to microbial activity can be calculated.

That is, as shown in FIG. 8, the intensity of the detected infrared energy is essentially constant except at the wavelength of 2.004 micrometers, which corresponds to one of the wavelengths at which carbon dioxide gas absorbs the infrared light. For the first reading, the decrease in intensity is only slight. However, the decrease in detected infrared light intensity at the absorption wavelength becomes greater for each reading, which indicates that a higher concentration of carbon dioxide exits in this particular sample vial 114 for each subsequent reading. The computer 152 interprets this trend as an indication that a carbon dioxide emitting organism is growing in the sample culture in the sample vial 114. The incubation and measurement module 102 can therefore report a positive sample growth for the sample culture contained in this particular sample vial 114.

As mentioned above, the detector assemblies 116 of the incubation and detection modules 102 are also capable of using the techniques described above, such as infrared diode laser spectroscopy, to quantify the concentration of oxygen gas in the head space of the sample vials 114 to detect a microorganisms' metabolic activity. As can be appreciated by one skilled in the art, some organisms are more easily detected by their consumption of oxygen.

When the incubation and measurement module 104 is being operated to detect gas phase oxygen in the sample vials 114, the reading controller controls the motor and pulley assembly 121 to translate the movable assembly 118 past the sample vials 114 to take readings in a manner similar to that described above for carbon dioxide. When the computer 152 determines, based on a detection signal provided by sensor 125, that the laser 132 for detecting oxygen gas is positioned at the appropriate location with respect to a first sample vial 114 to be read, computer 152 controls a laser 132 to emit infrared laser light at an output wavelength within a discrete band of wavelength that can be absorbed by oxygen. In this example, the wavelength of the emitted infrared laser light is in the 761.5 nanometer band.

Figure 9:
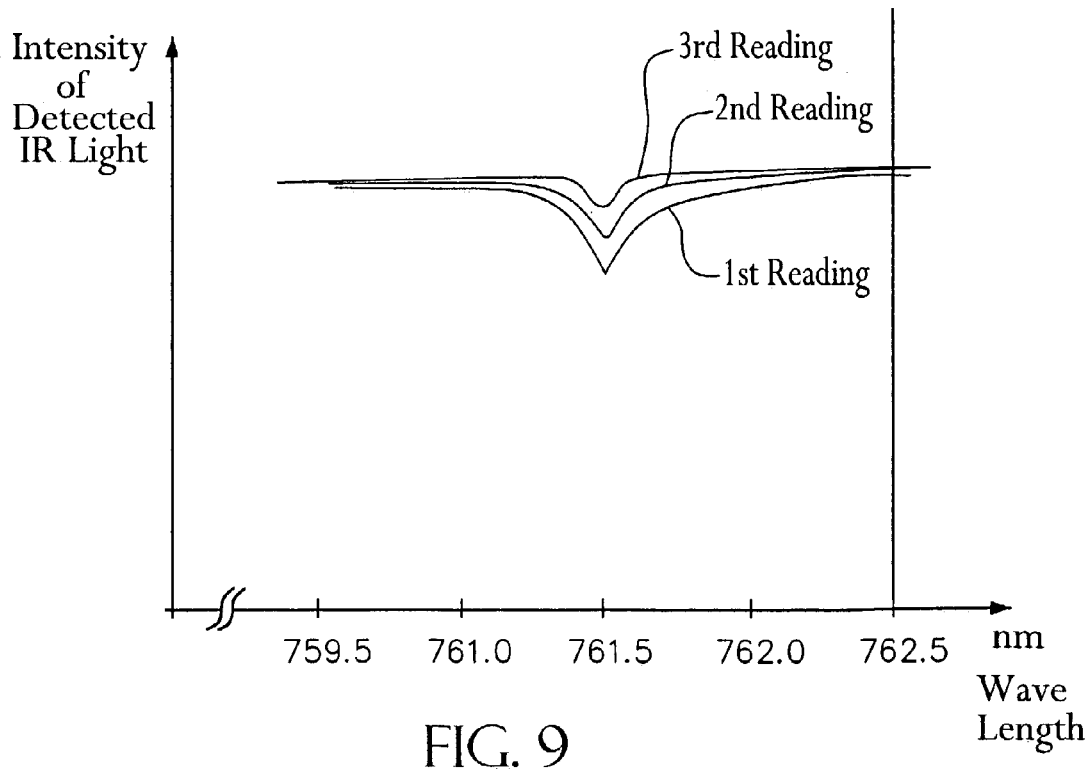
FIG. 9 is a graph illustrating an example of the intensity of the energy passing through the sample vial that is detected by the detector versus the wavelength of the detected energy, with an absorption peak being present at the wavelength at which oxygen absorbs the energy.

The infrared laser light thus passes through an enclosed volume of gas contained in the sample vial 114 in the area of the interior of the sample vial 114 above the microbial culture media. The computer 152 controls the detector 140 associated with laser 132 to detect the infrared laser light that passes through the sample vial 114. As described above, the detector 140 converts the detected infrared light into signals that are amplified by AC preamplifier 156, DC preamplifier 158 and lock-in amplifier 160, and that are then provided to computer 152. As with the readings for carbon dioxide, the computer 152 can represent the detected infrared signal graphically as shown in FIG. 9, with the detected intensity on the vertical axis versus wavelength on the horizontal axis.

As for the carbon dioxide readings described above, the reading controller can continue to control movement of the movable assembly 118 to take additional readings of the sample vials 114 at desired intervals in time. As the readings are taken, levels of oxygen concentration and change over time related to microbial activity can be calculated. That is, as shown in FIG. 9, the intensity of the detected infrared energy is essentially constant except at the wavelength of 761.5 nanometers, which corresponds to the wavelength at which oxygen gas absorbs the infrared light. For the first reading, the decrease in intensity is significant. However, the decrease in detected infrared light intensity at the absorption wavelength becomes less for each reading, which indicates that a lower concentration of oxygen exists in this particular sample vial 114 for each subsequent reading. The computer 152 interprets this trend as an indication that an oxygen consuming organism is growing in the sample culture in the sample vial 114.

The infrared diode laser spectroscopy techniques described above can also be used to quantify gas pressure in the head space above a liquid growth medium for the detection of microorganisms. As can be appreciated by one skilled in the art, organism or cell growth may be detected and observed by monitoring the change in a sealed vessel's gas pressure during the growth phase and life cycle. The computer 152 can thus measure the width of an absorption peak for a selected gas species, such as carbon dioxide or oxygen, or any of the other gases mentioned above, contained in the volume of gas in the sample vial 114, to detect for the presence of an oxygen consuming or carbon dioxide emitting organism. At a constant temperature, as pressure increases in this gas volume, the width of the absorption peak increases. As pressure decreases in this gas volume, the width of the absorption peak decreases. Monitoring these changes in absorption peak width over time characterizes the evolution of gas by the microorganisms or cells, and thus provides an indication of their growth. In addition, the gas species which is changing in the culture vessel is not critical to the detection of growth as any pressure changes effect the other gases present equally.

Accordingly, using the graph shown in FIG. 8 as an example, it can be seen that the width W1 of the absorption peak for the third reading is larger than the width W2 of the absorption peak for the first reading. The computer 152 interprets this increase in width as an increase in pressure in the sample vial 114. The incubation and measurement module 102 can therefore report a positive sample growth for the sample culture contained in this particular sample vial 114.

Although a broad spectrum light source such as the infrared radiation produced by a light bulb filament can be used to measure the absorption of light by various gases, it is not as sensitive or selective as a diode laser. The discrete absorption functions exhibited by a mixture of gases lie too close together to resolve with a broad spectrum source. A narrow band, single mode laser can produce light of one wavelength to measure a specific gas in a mixture of gases. Also, the amount of light absorbed at one wavelength is very small. Only a small fraction of a wide spectrum source is absorbed so detecting that effect is difficult. A laser on the other hand emits all of its light at one wavelength which if tuned to the desired absorption feature of a particular gas can be easily measured. Also, detection of the analyte itself (e.g., carbon dioxide, oxygen or any of the other gases mentioned above), rather than a byproduct of its presence, such as pH in the indicator techniques described in the Background section above, provides additional advantages in sensitivity and broad application.

Furthermore, the techniques described above are not limited to use with a particular type of sample vial. Rather, sample vial 114 can by any of the various types of culture vessels capable of containing the growth media. The sample vials 114 also can use various types of growth media to allow for detection and observation of the growth of mammalian cells, insect cells, bacteria, virus, mycobacteria, fungi, and other organisms which produce or consume gases as part of their growth and life cycle. The sample vials 114 can include a gas permeable membrane, slug, aliquot, or target which permits the optical interrogation of the gas signal and excludes intervening liquids or solids.

The above carbon dioxide, oxygen and other gas detection techniques can also be used to test if materials which are designed to be sterile are indeed free of contamination or infection with any of the organisms listed above. Examples of materials which may be tested includes processed foods, biological preparations such as banked human blood, mammalian cell lines and prepared injectables.

The combined use of IR spectroscopy for the detection of carbon dioxide and oxygen, as well as other gases, can also be used to enhance growth detection, provide presumptive speciation, and to separate background metabolism such as that caused by blood cells from bacterial or other cells. The techniques described above could also be used to determine the quantity of oxygen, carbon dioxide gas or other gases flushed into sealed containers as a preservative or stabilizer to maintain a product's shelf life or quality, or to detect immediate gas concentrations within a gas stream used, for example, in a production supply line. The pressure detecting technique described above could also be used to determine gas pressure in sealed containers that must be controlled to maintain a product's shelf life or quality.

Figure 10:
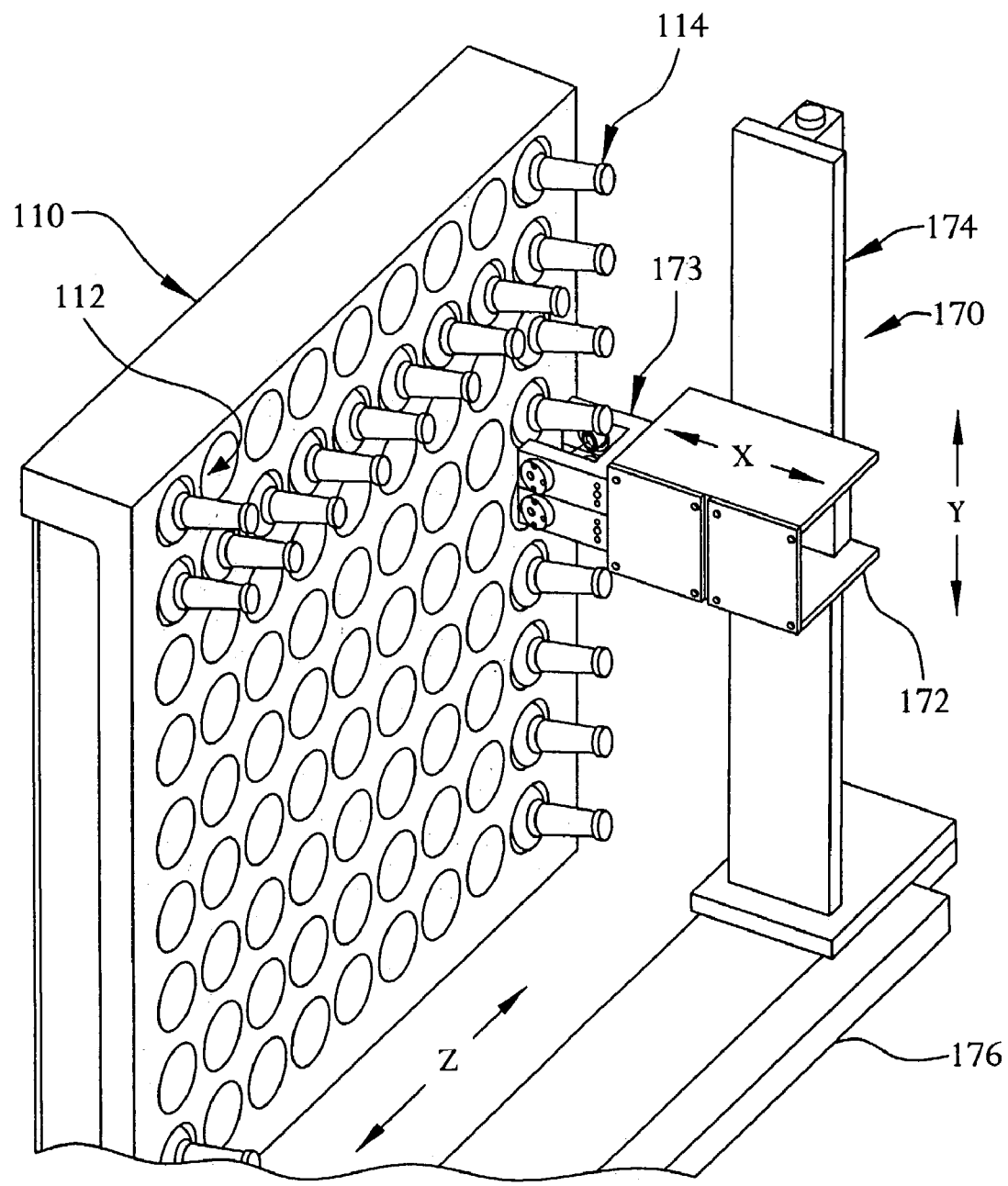
FIG. 10 is a block diagram of an example of another type of monitoring assembly that can be employed in the instrument shown in FIGS. 2 and 3.
Figure 11:
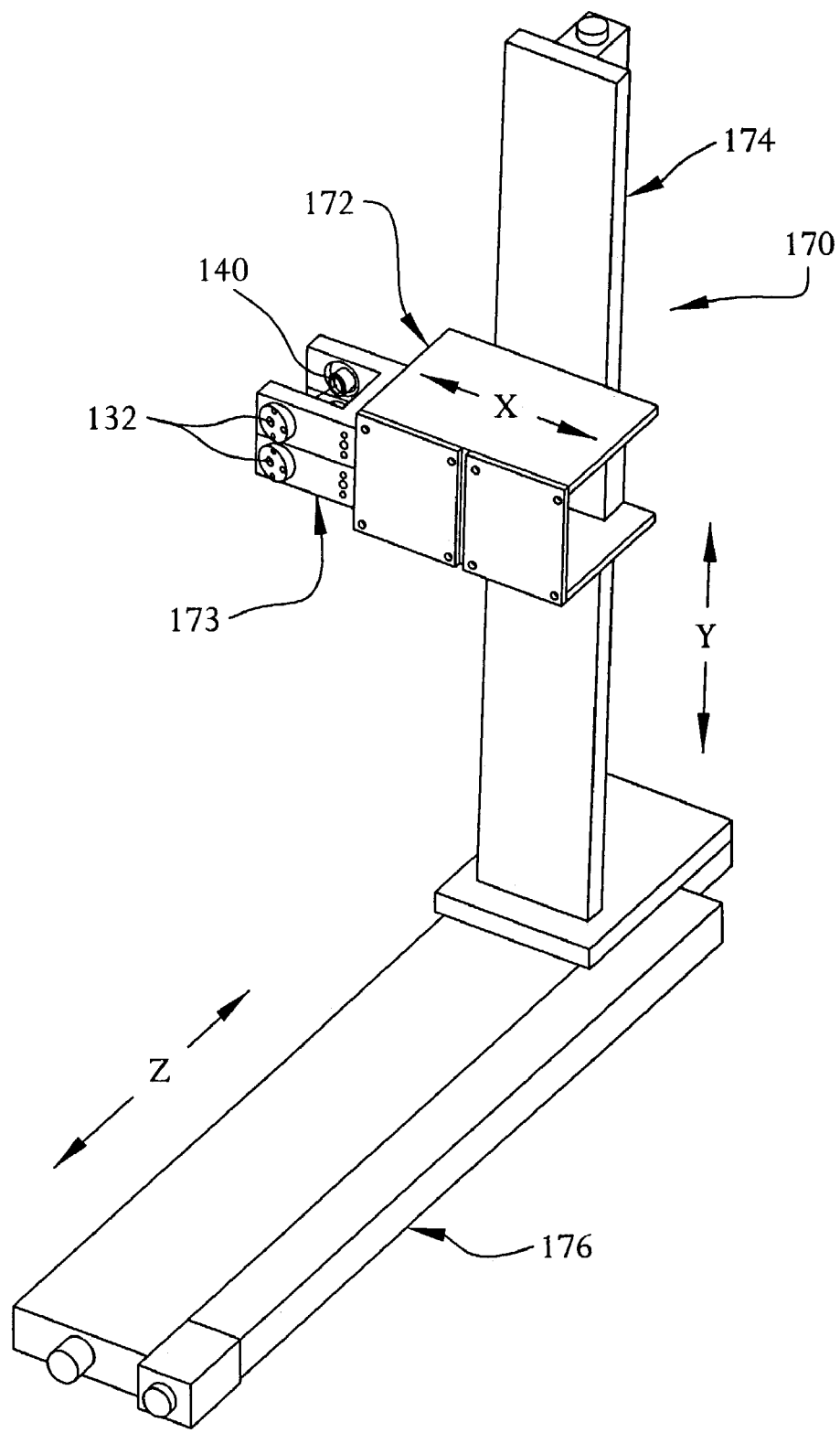
FIG. 11 is another block diagram of the monitoring assembly shown in FIG. 10.

An example of another type of monitoring assembly 170 will now be discussed with regard to FIGS. 10-15. As shown in FIGS. 10 and 11, the monitoring assembly 170 includes a sensor head housing 172 which houses a sensor assembly 173 that includes the types of lasers 132 and detectors 140 discussed above. In this example, sensor assembly 173 includes two lasers 132 and two corresponding detectors 140. However, sensor assembly 173 can be modified to include any desired number of lasers 132 and detectors 140.

Sensor head housing 172 is movably mounted to a vertical shaft 174 and can be moved in the "Y" direction along the vertical shaft 174 by, for example, a motor and pulley arrangement (not shown) or any other type of arrangement as can be appreciated by one skilled in the art. As further illustrated, vertical shaft 174 is movably mounted to a horizontal shaft 176, and can be moved along the "Z" direction along horizontal shaft 176 by a motor or pulley assembly (not shown) or any other type of arrangement as can be appreciated by one skilled in the art. As shown in FIG. 12, monitoring assembly 170 can be mounted in a module 102 between the two shelves 110 so that the sensor assembly 173 can take readings from sample vials 114 in both shelves 110 as described in more detail below.

As further shown in more detail in FIGS. 14 and 15, the sensor assembly 173 is movably mounted in sensor head housing 172 so that sensor assembly 173 can be retracted into the sensor head housing 172 along the "X" axis by a motor and gear or pulley arrangement (not shown), or by any other type of arrangement as can be appreciated by one skilled in the art. As shown in FIG. 15, the sensor assembly 173 can be further moved along the "X" direction to extend out of the other side of sensor head housing 172.

Figure 13:
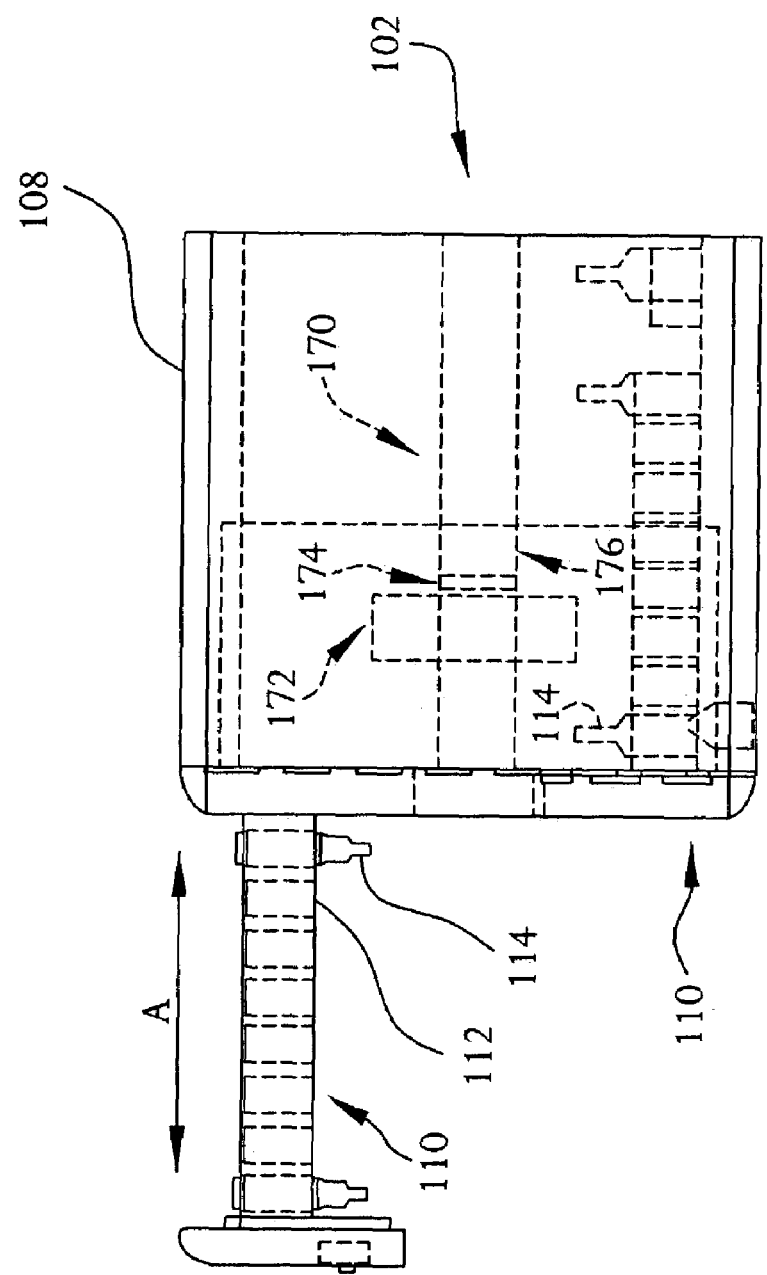
FIG. 13 is a detailed view of an example of a sensor head assembly employed in the monitoring assembly shown in FIGS. 10 and 11.
Figure 16:
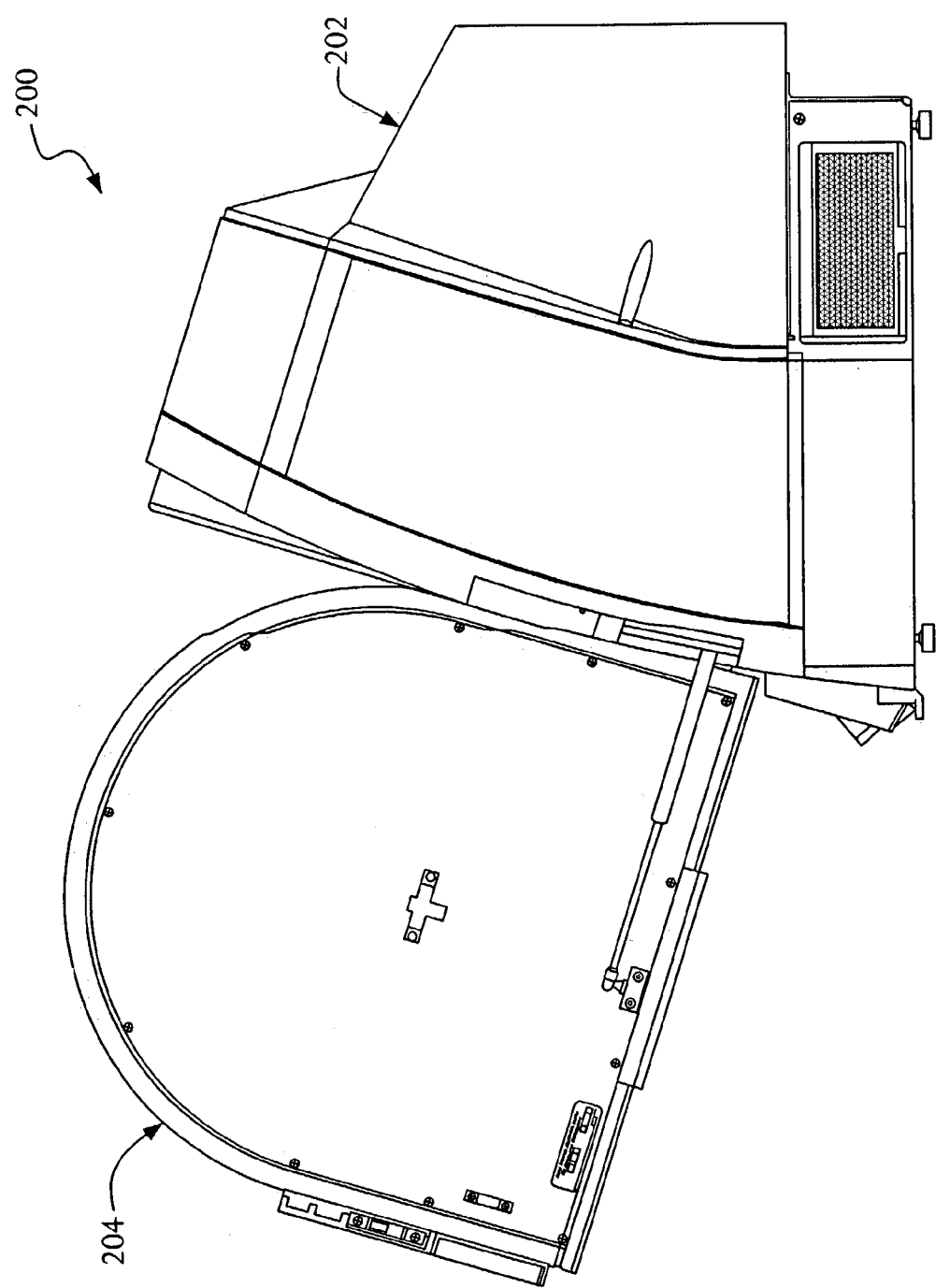
FIG. 16 is a side view of another type of instrument employing another embodiment of a detector assembly which uses infrared laser spectrography and dual wavelength modulation techniques to monitor the concentration of a gas or the pressure in sample vials according to another embodiment of the present invention.

Accordingly, when the monitoring assembly 170 is positioned in module 102 between the two shelves 110 as shown in FIG. 13, the computer 152 (see FIG. 7) can control movement of the sensor head housing 172, as well as the extension of the sensor assembly 173, so that the lasers 132 and detectors 140 can be positioned to take readings from the sample vials 114 in one of the shelves 110 as shown, for example, in FIG. 10. That is, the sensor head housing 172 can be aligned with one column of sample vials 114 and moved along the "Y" direction to take readings from that column of sample vials 114. The sensor assembly 173 can then be retracted into the sensor head housing 172 as shown in FIG. 14 so that the vertical shaft 174 and sensor head housing 172 can be moved in the "Z" direction to be aligned with another column of sample vials 114. The reading process can then be repeated to take readings from that column of sample vials 114, and the retracting, moving and reading process can be repeated for all columns of sample vials 114.

Once readings have been taken from all of the sample vials 114 in all of the columns in shelf 110, the computer 152 can control the monitoring assembly 170 to take readings from the sample vials 114 in the opposite shelf 110 in a similar manner. In this event, the computer 152 controls the monitoring assembly 170 to position the sensor head housing 172 for reading a column of sample vials 114 in that shelf 110. Once the sensor head housing 172 has been properly positioned, the computer 152 can control the sensor head housing 172 to extend the sensor assembly 173 from the opposite end of the sensor head housing 172 as shown in FIG. 15. The computer 152 then controls the sensor head housing 172 to move along the vertical shaft 174 so that the sensor assembly 173 can take readings from all the sample vials 114 in that column in a manner similar to that described above.

Once all of the sample vials 114 in that column have been read, computer 152 controls the sensor head housing 172 to retract the sensor assembly 173 as shown in FIG. 14. The computer 152 then controls movement of the vertical shaft 174 and sensor head housing 172 in the "Z" direction along horizontal shaft 176 until the sensor head housing 172 is positioned to read another column of sample vials 114. The sensor head housing 172 is then moved in the "Y" direction along vertical shaft 174 as appropriate to take readings from the sample vials 114 in that column of sample vials 114. The process is then repeated until readings have been taken from the sample vials 114 in all of the columns of that second shelf 110. Once all of the readings have been taken, the data can be processed, displayed and analyzed in a manner discussed above with regard to FIGS. 8 and 9.

In the arrangements discussed above, the light emitting devices and sensors move with respect to the containers. However, it is noted that the apparatus can be configured so that the containers are housed in a rotor, drum, conveyor or the like and controlled to move past the light emitting devices and sensors which remain stationary. In this arrangement, the containers are thus sensed as they move between the light emitting devices and sensors, and the readings obtained representing the contents of the containers are evaluated in the manners described above.

That is, as shown in FIGS. 16-20, an instrument 200 can employ a stationary monitoring assembly as will now be described. Specifically, instrument 200 includes a housing 202 and a door 204 that is coupled to the housing 202 by a hinge 206 and a piston arrangement 208 to provide access to the interior chamber of the housing 202. As discussed above with regard to a module 102, instrument 200 can act as an incubation chamber to incubate the samples stored in the sample vials 114.

Figure 17:
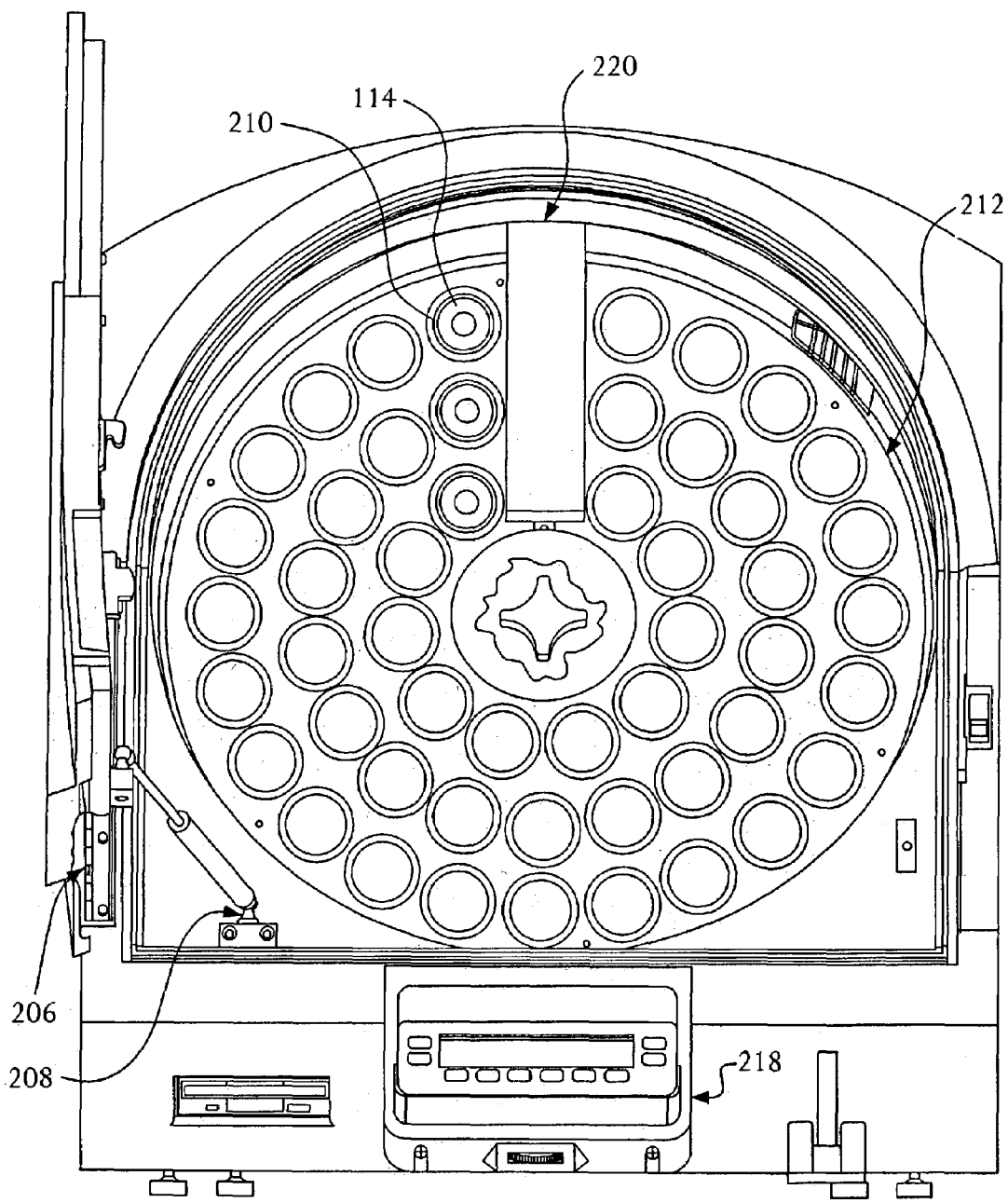
FIG. 17 is a front view of the instrument shown in FIG. 16.
Figure 18:
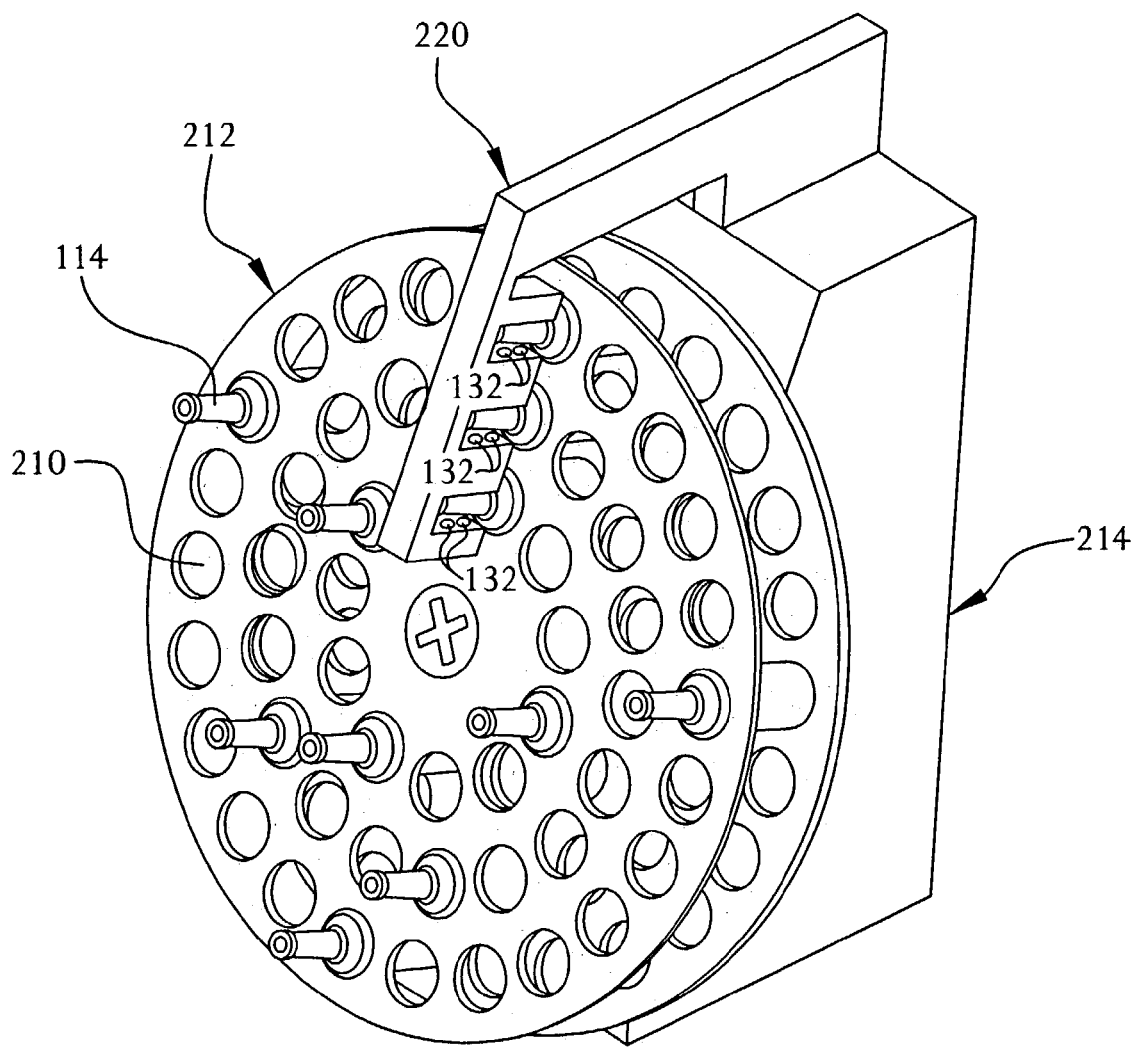
FIG. 18 is a detailed perspective view of the carousel and detector assembly arrangement in the instrument shown in FIGS. 16 and 17.
Figure 19:
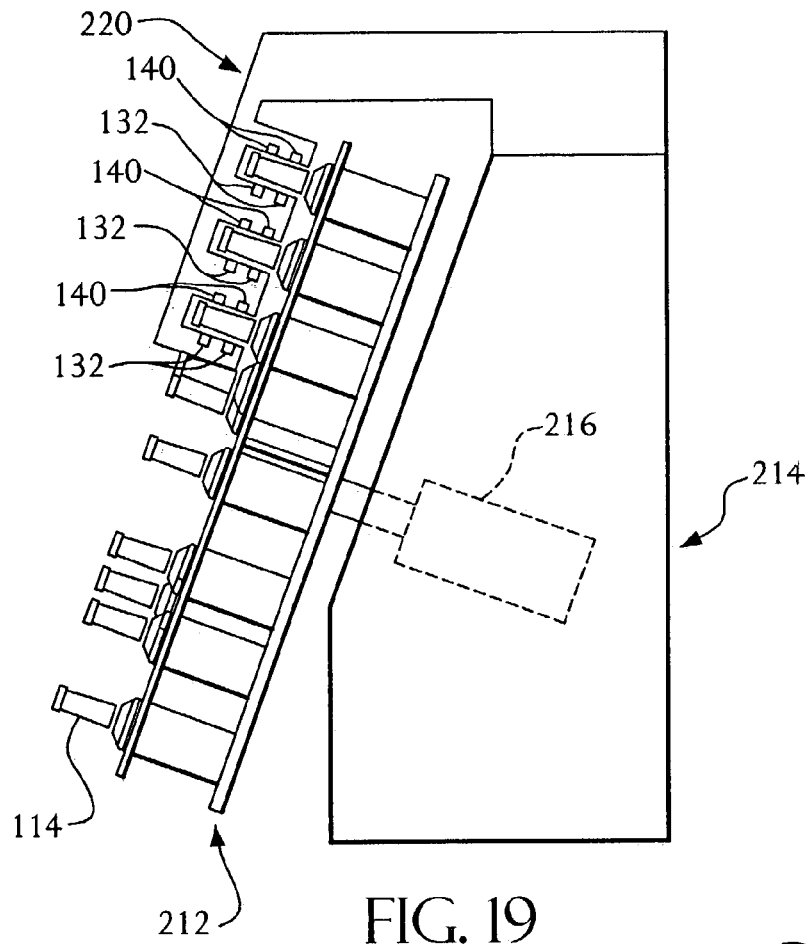
FIG. 19 is a side view of the carousel and detector head arrangement shown in FIG. 18.
Figure 20:
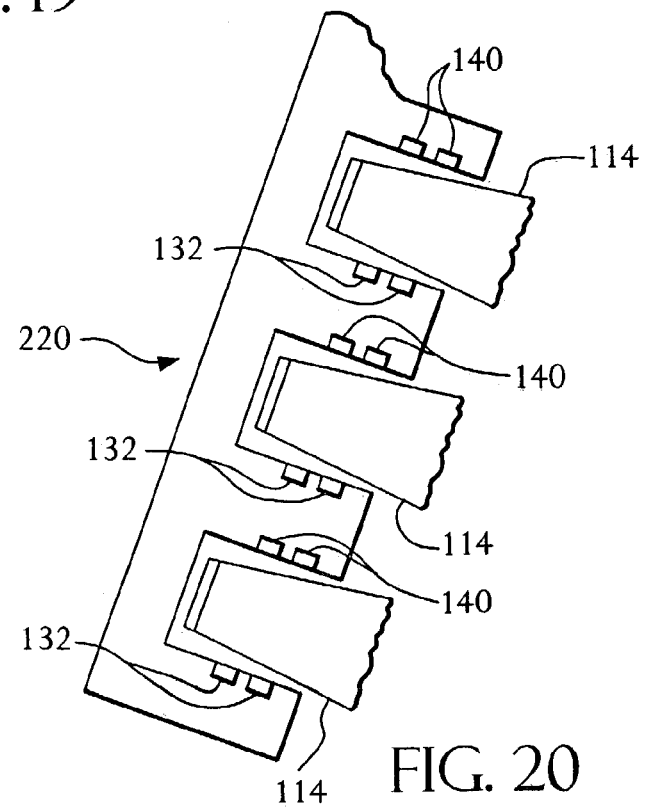
FIG. 20 is a detailed view of the detector assembly arrangement as shown in FIGS. 18 and 19.

As shown in FIGS. 17-19, sample vials 114 are loaded into openings 210 of a carousel 212. The carousel 212 is rotatably mounted to a carousel mount 214, which are both housed in the interior chamber of the housing 202. The carousel is operable by a motor 216 under the control of a controller (not shown), such as the type of controller described above, to rotate in a clockwise or counter clockwise direction, as desired. The instrument 200 further includes a control panel 218 which enables an operator to set the parameters of the instrument 200, such as the incubation temperature, speed of rotation of the carousel 212, and so on.

As further shown in FIGS. 17-20, instrument 200 includes a stationary monitoring assembly 220 that is mounted to the carousel mount 214 and is used to monitor the samples in the sample vials 114 in the manner similar to that described above. However, instead of the monitoring assembly 220 moving with respect to the sample vials 114, the carousel 212 rotates the sample vials 114 past the respective lasers 132 and detectors 140 so that the lasers 132 can emit laser light as described above through the respective necks of the sample vials 114. The lasers 132 and detectors 140 are coupled to the type of circuitry shown, for example, in FIG. 7, and described above. Accordingly, as the carousel 212 is rotated to move the sample vials 114 past their respective lasers 132 and detectors 140, the concentration of gas, such as oxygen or carbon dioxide in the sample vials 114, or the pressure in the sample vials 114, is monitored in the manner described above, and thus the concentration of sample growth can be monitored in the manner described above.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for detecting the growth of microorganisms in a sample in a container, comprising:
   an apparatus comprising:
      a module comprising a plurality of openings configured for receiving sample containers;
      a detector unit comprising a plurality of lasers each of which emit radiation at a substantially single wavelength, that wavelength being one at which a gas selected from the group consisting of $O_2$, $CO_2$, $NH_3$, $H_2S$ and $CH_4$ absorbs radiation, said substantially single wavelength at which $CO_2$ absorbs radiation being approximately 2.004 micrometers, and wherein at least a first laser emits radiation at a wavelength that is different from at least one other laser and a plurality of detectors, each of which is associated with a laser wherein each detector detects at least a portion of said radiation emitted from its associated laser, and wherein the detectors are positioned relative to the lasers such that a gas-containing portion of the sample containers can pass between said laser and said detector;
   a signal analyzer that analyzes said detected radiation from said plurality of lasers to determine a parameter from a plurality of said gases, said parameter selected from the group consisting of the pressure of the gas in the container, the concentration of the gas in the container and the presence of the gas in the container; and
   sample containers that are substantially optically transparent at said emission wavelength of said plurality of lasers and wherein said detector unit further comprises a housing, said plurality of lasers and said plurality of detectors being movably disposed within said housing, said housing being movable such that said lasers and said detectors are capable of being located proximate to each of said containers.

2. The system of claim 1, wherein said containers are arranged in a plurality of rows and columns, and said housing is adapted to move along said rows and said columns.

3. The system of claim 2, wherein said housing is adapted to extend said laser and said detector toward each said container and to retract said laser and said detector away from each said container.

* * * * *